US010179846B1

(12) United States Patent
Crall et al.

(10) Patent No.: US 10,179,846 B1
(45) Date of Patent: Jan. 15, 2019

(54) SELF-HEALING POLYMERIC MATERIAL SYNTHESIZED BY GUIDING MAGNETIC MICROCAPSULES

(71) Applicant: The University of Tulsa, Tulsa, OK (US)

(72) Inventors: Matthew D. Crall, Little Rock, AR (US); Michael W. Keller, Tulsa, OK (US)

(73) Assignee: The University of Tulsa, Tulsa, OK (US)

( * ) Notice: Subject to any disclaimer, the term of this patent is extended or adjusted under 35 U.S.C. 154(b) by 4 days.

(21) Appl. No.: 15/612,256

(22) Filed: Jun. 2, 2017

Related U.S. Application Data

(60) Provisional application No. 62/344,707, filed on Jun. 2, 2016.

(51) Int. Cl.
C08K 9/06 (2006.01)
C08K 3/16 (2006.01)
C08K 9/10 (2006.01)
B01J 13/18 (2006.01)
H01F 1/03 (2006.01)

(52) U.S. Cl.
CPC ............ *C08K 3/16* (2013.01); *B01J 13/18* (2013.01); *C08K 9/06* (2013.01); *C08K 9/10* (2013.01); *H01F 1/0302* (2013.01); *C08K 2201/01* (2013.01); *C08K 2201/011* (2013.01)

(58) Field of Classification Search
CPC ..... C08K 3/16; C08K 9/06; C08K 9/10; B01J 13/18
See application file for complete search history.

(56) References Cited

U.S. PATENT DOCUMENTS

| 5,972,493 | A | * | 10/1999 | Iwasaki | ............... B43L 1/008 428/323 |
|---|---|---|---|---|---|
| 7,569,625 | B2 | | 8/2009 | Keller et al. | |
| 2009/0191402 | A1 | | 7/2009 | Beiermann et al. | |

OTHER PUBLICATIONS

Caruso, M.M., et al; Full Recovery of Fracture Toughness Using a Nontoxic Solvent-Based Self-Healing System; Advanced Functional Materials 2008, 18 (13), 1898-1904.
Brown, E.N., et al; Microcapsule Induced Toughening in a Self-healing Polymer Composite; Journal of Materials Science 2004, 39 (5), 1703-1710.
White, S.R., et al; Autonomic Healing of Polymer Composites; Nature 2001, 409 (6822), 794-797.
Rule, J.D., et al; Effect of Microcapsule Size on the Performance of Self-healing Polymers; Polymer 2007, 48 (12), 3520-3529.
Trask, R.S., et al; Bioinspired Self-Healing of Advanced Composite Structures Using Hollow Glass Fibres; Journal of the Royal Society Interface 2007, 4 (13), 363-371.
Patrick, J.F., et al; Continuous Self-Healing Life Cycle in Vascularized Structural Composites; Advanced Materials 2014, 26 (25), 4302-4308.
Krull, B.P., et al; Strategies for Volumetric Recovery of Large Scale Damage in Polymers; Advanced Functional Materials 2016, 26, 4561-4569.
Li, C.-H, et al; A Highly Stretchable Autonomous Self-Healing Elastomer; Nature Chemistry 2016, 8 (6), 618-624.
Brown, E.N., et al; in Situ Poly(urea-formaldehyde) Microencapsulation of Dicyclopentadiene; Journal of Microencapsulation 2003, 20 (6), 719-730.
Caruso, M.M., et al; Robust, Double-Walled Microcapsules for Self-Healing Polymeric Materials; ACS Applied Materials and Interfaces 2010, 2 (4), 1195-1199.
Kang, S., et al; Core-Shell Polymeric Microcapsules with Superior Thermal and Solvent Stability; ACS Applied Materials and Interfaces 2015, 7 (20), 10952-10956.
Yuan, L., et al; Preparation and Characterization of Poly(urea-formaldehyde) Microcapsules Filled with Epoxy Resins; Polymer 2006, 47 (15), 5338-5349.
Cho, S.H., et al; Self-Healing Polymer Coatings; Advanced Materials 2009, 21 (6), 645-649.
Loiseau, E., et al; Explosive Raspberries: Controlled Magnetically Triggered Bursting of Microcapsules; Advanced Functional Materials 2016, 26 (22), 4007-4015.
Bolimowski, P.A., et al; Robust Synthesis of Epoxy Resin-filled Microcapsules for Application to Self-Healing Materials; Philosophical Transactions of the Royal Society A: Mathematical, Physical and Engineering Sciences 2016, 374 (2061).
Laurent, S., et al; Superparamagnetic Iron Oxide Nanoparticles for Delivery of Therapeutic Agents: Opportunities and Challenges; Expert Opinion on Drug Delivery 2014, 11 (9), 1449-1470.
Mody, V.V., et al; Magnetic Nanoparticle Drug Delivery Systems for Targeting Tumor; Applied Nanoscience 2014, 4 (4), 385-392.
Erb, R.M., et al; Composites Reinforced in Three Dimensions by Using Low Magnetic Fields; Science 2012, 335 (6065), 199-204.
Erb, R.M., et al; Locally Reinforced Polymer-Based Composites for Elastic Electronics; ACS Applied Materials & Interfaces 2012, 4 (6), 2860-2864.
Sommer, M.R., et al; Injectable Materials with Magnetically Controlled Anisotropic Porosity; ACS Applied Materials & Interfaces 2012, 4 (10), 5086-5091.
Lin, Z., et al; Magnetic Alignment of Hexagonal Boron Nitride Platelets in Polymer Matrix: Toward High Performance Anisotropic Polymer Composites for Electronic Encapsulation; ACS Applied Materials & Interfaces 2013, 5 (15), 1633-7640.

(Continued)

*Primary Examiner* — Hannah J Pak
(74) *Attorney, Agent, or Firm* — Head, Johnson, Kachigian & Wilkinson, PC

(57) ABSTRACT

A process of making magnetic microcapsules and a process of making polymeric material having self-healing properties. The process of making polymeric material having self-healing properties includes the steps of mixing microcapsules containing magnetic nanoparticles in a liquid polymer before curing, and guiding the microcapsules in the liquid polymer before curing by magnetic forces to a desired location or locations. Finally, the liquid polymer with the microcapsules is cured to a solid polymeric material.

17 Claims, 14 Drawing Sheets

(56) References Cited

OTHER PUBLICATIONS

Gaska, K., et al; Magnetic-aligned, Magnetite-filled Epoxy Composites with Enhanced Thermal Conductivity; Journal of Materials Science 2015, 50 (6), 2510-2516.

Kokkinis, D., et al; Multimaterial Magnetically Assisted 3D Printing of Composite Materials; Nature Communications 2015, 6, 8643.

Fragouli, D., et al; Nanocomposite Pattern-Mediated Magnetic Interactions for Localized Deposition of Nanomaterials; ACS Applied Materials & Interfaces 2013, 5 (15), 7253-7257.

Tokarev, A., et al; Reconfigurable Anisotropic Coatings via Magnetic Field-Directed Assembly and Translocation of Locking Magnetic Chains; Advanced Functional Materials 2014, 24 (30), 4738-4745.

Zhu, G., et al; Flexible Magnetic Nanoparticles-Reduced Graphene Oxide Composite Membranes Formed by Self-Assembly in Solution; ChemPhysChem 2010, 11 (11), 2432-2437.

Jalali, M., et al; Electromagnetic Shielding of Polymer-Matrix Composites with Metallic Nanoparticles; Composites Part B: Engineering 2011, 42 (6), 1420-1426.

Hetti, M., et al; Magnetite Core-Shell Nanoparticles in Nondestructive Flaw Detection of Polymeric Materials; ACS Applied Materials & Interfaces 2016, 8, 28208-28215.

Zhao, Y., et al; Magnetic Liquid Marbles: Manipulation of Liquid Droplets Using Highly Hydrophobic Fe3O4 Nanoparticles; Advanced Materials 2010, 22 (6), 707-710.

Fang, M., et al; Rapid Mixing: A Route to Synthesize Magnetite Nanoparticles with High Moment; Applied Physics Letters 2011, 99, 222501-3.

Stober, W., et al; Controlled Growth of Monodisperse Silica Spheres in the Micron Size Range; Journal of Colloid and Interface Science 1968, 26 (1), 62-69.

Laurent, S., et al; Magnetic Iron Oxide Nanoparticles: Synthesis, Stabilization, Vectorization, Physicochemical Characterizations, and Biological Applications; Chemical Reviews 2008, 108 (6), 2064-2110.

Brown, E.N.; Use of the Tapered Double-Cantilever Beam Geometry for Fracture Toughness Measurements and Its Application to the Quantification of Self-Healing; The Journal of Strain Analysis for Engineering Design 2011, 46 (3), 167-186.

Hamoudeh, M., et al; Preparation, Characterization and Surface Study of Poly-epsilon Caprolactone Magnetic Microparticles; Journal of Colloid and Interface Science 2006, 300 (2), 584-590.

Aliahmad, M., et al; Synthesis of Maghemite (y-Fe2O3) Nanoparticles by Thermal-decomposition of Magnetite (Fe3O4) Nanoparticles; Materials Science—Poland 2013, 31 (2), 264-268.

Stephen, Z.R., et al; Magnetite Nanoparticles for Medical MR Imaging; Materials Today 2011, 14 (7-8), 330-338.

Brice-Profeta, S., et al; Magnetic Order in y-Fe2O3 Nanoparticles: a XMCD Study; Journal of Magnetism and Magnetic Materials 2005, 288, 354-365.

Sinks, B.; Particles as Surfactants—Similarities and Differences; Current Opinion in Colloid & Interface Science 2002, 7 (1-2), 21-41.

Jin, H., et al; Self-Healing Thermoset Using Encapsulated Epoxy-amine Healing Chemistry; Polymer 2012, 1-7.

Zhu, G., et al; Self-encapsulation of Epoxy Resin by a Controlled Interface Curing Process in Epoxy/Water Emulsion; ICSHM2013: Proceedings of the 4th International Conference on Self-Healing Materials, 230-234.

vLAISZIK, B.J., et al; Self-Healing Polymers and Composites; Annual Review of Materials Research 2010, 40, 179-211.

Li, Q., et Effects of Dual Component Microcapsules of Resin and Curing Agent on the Self-healing Efficiency of Epoxy; Composites: Part B 2013, 55, 79-85.

Leping, L., et al; Preparation and Characterization of Microcapsule Containing Epoxy Resin and Its Self-healing Performance of Anti-corrosion Covering Material; Chinese Science Bulletin 2011, 56 (4-5), 439-443.

Keller, M.; Encapsulation-Based Self-Healing Polymers and Composites; RSC Polymer Chemistry Series No. 5; Healable Polymer Systems, Chapter 2, 16-61.

\* cited by examiner

SELF-HEALING POLYMERIC MATERIAL SYNTHESIZED BY GUIDING MAGNETIC MICROCAPSULES

CROSS REFERENCE

This application claims priority to and the benefit of U.S. Provisional Patent Application Ser. No. 62/344,707, filed Jun. 2, 2016, which is herein incorporated in its entirety by reference.

FEDERALLY SPONSORED RESEARCH OR DEVELOPMENT

This invention was developed with the assistance of a National Science Foundation (NSF) grant (CMMI 1351760). The U.S. Government may have rights in this invention.

BACKGROUND OF THE INVENTION

Field of the Invention

The present invention is directed to a process of making magnetic microcapsules, to a process of making polymeric material having self-healing properties, and to self-healing polymeric materials synthesized by guiding magnetic microcapsules.

Description of the Related Art

Within the past 15 years, materials science has seen significant advances in the field of multi-functional materials. A subset of this field studies materials with the capability to self-repair, called self-healing materials. There are several mechanisms that can be used to achieve self-healing functionality. One particularly successful approach is to sequester a liquid "healing agent" in a material that can be delivered to autonomically repair damaged regions. [Trask R. S., Bond I. P., Williams G. J., & Williams H. R., "Bioinspired self-healing of advanced composite materials", Paper presented at the Collection of Technical Papers—AIAA/ASME/ASCE/AHS/ASC Structures, Structural Dynamics and Materials Conference, (2008)]. [Caruso M. M Blaiszik B. J., White S. R., Sottos N. R., and Moore J. S., "Full Recovery of Fracture Toughness Using a Nontoxic Solvent-Based Healing System", *Advanced Functional Materials*, 18, 1898-1904, (2008)]. [Rule J. D., Sottos N. R., White S. R., "Effect of Microcapsule Size on the Performance of Self-Healing Polymers", *Polymer*, 48, 3520-3529, (2007)]. Damage releases the liquid and this triggers the initiation of an autonomic repair. Healing agents can be delivered using vascular networks embedded in the material or through the use of liquids sequestered in microcapsules. The released healing agent may be pulled into the damage by capillary action. Healing can also be achieved using reversible molecular bands intrinsic to the matrix material itself [Li, C.-H.; Wang, C.; Keplinger, C.; Zuo, J.-L.; Jin, L.; Sun, Y.; Zheng, P.; Cao, Y.; Lissel, F.; Linder, C.; You, X.-Z.; Bao, Z., A highly stretchable autonomous self-healing elastomer. *Nat Chem* 2016, 8 (6), 618-624].

Many microcapsule-based self-healing materials are synthesized by simply mixing in microcapsules into a host polymer before it cures. An approaching crack ruptures the embedded microcapsules and releases the healing agent. The microcapsules serve as both storage and trigger of the healing response. The healing agent then reacts and bonds the crack faces, restoring the fracture toughness of the material. [Caruso M. M., Blaiszik B. J., White S. R., Sottos N. R., and Moore J. S., "Full Recovery of Fracture Toughness Using a Nontoxic Solvent-Based Healing System", *Advanced Functional Materials*, 18, 1898-1904, (2008)]. [Rule J. D., Sottos N. R., White S. R., "Effect of Microcapsule Size on the Performance of Self-Healing Polymers", *Polymer*, 48, 3520-3529, (2007)].

Various types of microcapsules have been synthesized for these types of applications, including microcapsules with varying core and shell materials, shell thicknesses, and numbers of shell layers. These improvements serve either to make the microcapsules more robust or to expand the range of healing chemistries that can be used. [Brown E. N., Kessler M. R., Sottos N. R., & White S. R., "In situ poly(urea-formaldehyde) microencapsulation of dicyclopentadiene", *Journal of Microencapsulation*, 20(6), 719-730, (2003)—process to manufacture]. [Caruso M. M., Blaiszik B. J., Jin H., Schelkopf S. R., Stradley D. S., Sottos N. R., Moore J. S. "Robust, double-walled microcapsules for self-healing polymeric materials", *ACS Applied Materials and Interfaces*, 2(4), 1195-1199, (2010)]. [Kang S., Baginska M., White S. R., & Sottos N. R., "Core-Shell Polymeric Microcapsules with Superior Thermal and Solvent Stability", *ACS Applied Materials and Interfaces*, 7(20), 10952-10956, (2015)]. Such developments are geared towards creating intelligently designed materials with unique properties desirable for specific applications.

While microcapsules enable self-healing functionality, the inclusion of microcapsules in polymeric materials can alter material properties in several ways. Typically, as microcapsule concentration increases, fracture toughness increases, as should be expected for the inclusion of particles in the matrix. [Brown E. N., White S. R., Sottos N. R., "Microcapsule induced toughening in a self-healing polymer composite", *Journal of Materials Science*, 39, 1703-1710, (2004)]. In contrast, overall material modulus and ultimate strength can decrease as microcapsules are added. [Brown E. N., White S. R., Sottos N. R., "Microcapsule induced toughening in a self-healing polymer composite", *Journal of Materials Science*, 39, 1703-1710, (2004)]. Therefore, in order to minimize the negative impact on material properties, it is desirable to develop techniques for optimizing concentration of the microcapsules in order to minimize cost and any negative impact on material properties.

One possible approach for mitigating negative impacts is to guide microcapsules to locations that have been identified as regions of high failure probability. This stands in stark contrast to current self-healing methods, which use systems which are universally dispersed throughout the material. The ability to guide the microcapsules to a specific location can reduce the total amount of healing components required to achieve self-healing and could lessen the impact on structural properties. This also has the potential to decrease the overall cost of the material by minimizing the required amount of high-cost chemicals, such as Grubbs' catalyst, that are used in many healing systems. [Brown, E. N.; White, S. R.; Sottos, N. R., Microcapsule induced toughening in a self-healing polymer composite. Journal of Materials Science 2004, 39 (5), 1703-1710]. [White, S. R.; Sottos, N. R.; Geubelle, P. H.; Moore, J. S.; Kessler, M. R.; Sriram, S. R.; Brown, E. N.; Viswanathan, S., Autonomic healing of polymer composites. Nature 2001, 409 (6822), 794-797]. [Brown, E. N.; Kessler, M. R.; Sottos, N. R.; White, S. R., In situ poly(urea-formaldehyde) microencapsulation of dicyclopentadiene. Journal of Microencapsulation 2003, 20 (6), 719-30].

This guiding can be accomplished using magnetic fields in a manner similar to targeted drug delivery methods being developed in biomedicine. [Laurent S., Saei A. A., Behzadi S., Panahifar A., & Mahmoudi M., "Superparamagnetic iron oxide nanoparticles for delivery of therapeutic agents: Opportunities and challenges", *Expert Opinion on Drug Delivery*, 11(9), 1449-1470, (2014)]. [Lin, Z.; Liu, Y.; Raghavan, S.; Moon, K.-s.; Sitaraman, S. K.; Wong, C.-p., Magnetic Alignment of Hexagonal Boron Nitride Platelets in Polymer Matrix: Toward High Performance Anisotropic Polymer Composites for Electronic Encapsulation. ACS Applied Materials & Interfaces 2013, 5 (15), 7633-7640]. [Gaska, K.; Kmita, G.; Rybak, A.; Sekula, R.; Goc, K.; Kapusta, C., Magnetic-aligned, magnetite-filled epoxy composites with enhanced thermal conductivity. Journal of Materials Science 2015, 50 (6), 2510-2516]. Typically, these types of systems use an "encapsulated" magnetic nanoparticle where a single solid particle core is coated in silica, which is then functionalized with biomarkers. These particles then preferentially attach to certain sites, such as tumors, after which the magnetic nature of the particles is used to aid in imaging or local heating. [Gaska, K.; Kmita, G.; Rybak, A.; Sekula, R.; Goc, K.; Kapusta, C., Magnetic-aligned, magnetite-filled epoxy composites with enhanced thermal conductivity. Journal of Materials Science 2015, 50 (6), 2510-2516]. [Kokkinis, D.; Schaffner, M.; Studart, A. R., Multimaterial magnetically assisted 3D printing of composite materials. Nature Communications 2015, 6, 8643]. [Fragouli, D.; Torre, B.; Villafiorita-Monteleone, F.; Kostopoulou, A.; Nanni, G.; Falqui, A.; Casu, A.; Lappas, A.; Cingolani, R.; Athanassiou, A., Nanocomposite Pattern-Mediated Magnetic Interactions for Localized Deposition of Nanomaterials. ACS Applied Materials & Interfaces 2013, 5 (15), 7253-7257]. In materials science, magnetic nanoparticles are incorporated into materials to enhance desired properties such as electrical or thermal conductivity. [Tokarev, A.; Gu, Y.; Zakharchenko, A.; Trotsenko, O.; Luzinov, I.; Kornev, K. G.; Minko, S., Reconfigurable Anisotropic Coatings via Magnetic Field-Directed Assembly and Translocation of Locking Magnetic Chains. Advanced Functional Materials 2014, 24 (30), 4738-4745]. [Zhu, G.; Liu, Y.; Xu, Z.; Jiang, T.; Zhang, C.; Li, X.; Qi, G., Flexible Magnetic Nanoparticles—Reduced Graphene Oxide Composite Membranes Formed by Self-Assembly in Solution. ChemPhysChem 2010, 11 (11), 2432-2437].

One of the first successful instances of magnetic fields being used to alter a composite material was demonstrated by Erb et al. [Erb, R. M.; Libanori, R.; Rothfuchs, N.; Studart, A. R., Composites Reinforced in Three Dimensions by Using Low Magnetic Fields. Science 2012, 335 (6065), 199]. In this study, magnetic fields were used to preferentially orient magnetic particulate along primary directions to enhance structural properties over randomly oriented particulate reinforcement. They also demonstrated the ability to concentrate the particulate in areas of stress concentration. Other studies have used magnetic fields interacting with magnetic particles to create areas or directions of preferential stiffness, porosity, thermal conductivity or expansion, all by using magnetic fields to orient the particles along a desired direction. [Erb, R. M.; Cherenack, K. H.; Stahel, R. E.; Libanori, R.; Kinkeldei, T.; Münzenrieder, N.; Tröster, G.; Studart, A. R., Locally Reinforced Polymer-Based Composites for Elastic Electronics. ACS Applied Materials & Interfaces 2012, 4 (6), 2860-2864]. [Sommer, M. R.; Erb R. M.; Studart, A. R., Injectable Materials with Magnetically Controlled Anisotropic Porosity. ACS Applied Materials & Interfaces 2012, 4 (10), 5086-5091]. [Lin, Z.; Liu, Y.; Raghavan, S.; Moon, K.-s.; Sitaraman, S. K.; Wong, C.-p., Magnetic Alignment of Hexagonal Boron Nitride Platelets in Polymer Matrix: Toward High Performance Anisotropic Polymer Composites for Electronic Encapsulation. ACS Applied Materials & Interfaces 2013, 5 (15), 7633-7640]. [Gaska, K.; Kmita, G.; Rybak, A.; Sekula, R.; Goc, K.; Kapusta, C., Magnetic-aligned, magnetite-filled epoxy composites with enhanced thermal conductivity. Journal of Materials Science 2015, 50 (6), 2510-2516]. Similar methods have been used to orient particulate for improved 3D printing, multi-functional films for electronics, and self-assembly of coatings and membranes. [Kokkinis, D.; Schaffner, M.; Studart, A. R., Multimaterial magnetically assisted 3D printing of composite materials. Nature Communications 2015, 6, 8643]. [Erb, R. M.; Cherenack, K. H.; Stahel, R. E.; Libanori, R.; Kinkeldei, T.; Münzenrieder, N.; Tröster, G.; Studart, A. R., Locally Reinforced Polymer-Based Composites for Elastic Electronics. ACS Applied Materials & Interfaces 2012, 4 (6), 2860-2864]. [Fragouli, D.; Torre, B.; Villafiorita-Monteleone, F.; Kostopoulou, A.; Nanni, G.; Falqui, A.; Casu, A.; Lappas, A.; Cingolani, R.; Athanassiou, A., Nanocomposite Pattern-Mediated Magnetic Interactions for Localized Deposition of Nanomaterials. ACS Applied Materials & Interfaces 2013, 5 (15), 7253-7257]. [Tokarev, A.; Gu, Y.; Zakharchenko, A.; Trotsenko, O.; Luzinov, I.; Kornev, K. G.; Minko, S., Reconfigurable Anisotropic Coatings via Magnetic Field-Directed Assembly and Translocation of Locking Magnetic Chains. Advanced Functional Materials 2014, 24 (30), 4738-4745]. [Zhu, G.; Liu, Y.; Xu, Z.; Jiang, T.; Zhang, C.; Li, X.; Qi, G., Flexible Magnetic Nanoparticles-Reduced Graphene Oxide Composite Membranes Formed by Self-Assembly in Solution. ChemPhysChem 2010, 11 (11), 2432-2437]. Additionally, magnetic particles have been used to create composites with unique bulk properties for electromagnetic shielding, surface flaw detection, or controlled rupture of internal microcontainers. [Jalali, M.; Dauterstedt, S.; Michaud, A.; Wuthrich, R., Electromagnetic shielding of polymer-matrix composites with metallic nanoparticles. Composites Part B: Engineering 2011, 42 (6), 1420-1426]. [Hetti, M.; Wei, Q.; Pohl, R.; Casperson, R.; Bartusch, M.; Neu, V.; Pospiech, D. U.; Voit, B., Magnetite Core-Shell Nanoparticles in Nondestructive Flaw Detection of Polymeric Materials. ACS Applied Materials & Interfaces 2016]. [Loiseau, E.; de Boiry, A. Q.; Niedermair, F.; Albrecht, G.; Rühs, P. A.; Studart, A. R., Explosive Raspberries: Controlled Magnetically Triggered Bursting of Microcapsules. Advanced Functional Materials 2016, 26 (22), 4007-4015].

All of these materials use the mechanical, electrical, or thermal properties of the magnetic particle itself to alter bulk material properties. If the orientation or location of the particle is intentionally set using magnetic fields, then improvement can be seen over using the particulate as a randomly oriented or distributed additive.

In the present invention, magnetic particles are used to alter the self-healing performance of a material. Here the magnetic particles serve as the active material that allows self-healing components to be assembled into structures that were previously not possible. This required the development of a novel type of magnetic microcapsule containing magnetic particles suspended in a liquid core. This is different from other "encapsulated" nanoparticles where the particle is a solid core with a solid shell. The presence of these magnetic particles in the liquid core allows the accurate manipulation of the microcapsule location within the material using magnetic fields.

The present invention provides a process of making magnetic microcapsules.

The present invention also details the synthesis and performance of such magnetic microcapsules in a self-healing polymer.

The present invention also provides a process to guide microcapsules to a desired location or locations in a polymer using magnetic fields. Targeted placement is achieved by rendering microcapsules responsive to magnetic fields through encapsulation of magnetic nanoparticles suspended in a healing agent.

SUMMARY OF THE INVENTION

In a first aspect, the present invention relates to a process of making magnetic microcapsules. This process includes the steps of coating magnetic particles which are micron or smaller size with a hydrophobic material coating to form nanoparticles. The nanoparticles are thereafter suspended in a core material. The core material and the nanoparticles are then encapsulated in an outer wall to form magnetic microcapsules.

In one embodiment, the magnetic particles may be fabricated from an iron salt solution. The hydrophobic material for the magnetic particles coating may be silane.

The outer wall encapsulating the core material and nanoparticles may be achieved in a variety of ways. In one preferred embodiment, the outer wall may be formed from a reaction with urea-formaldehyde. Other possibilities include a polyurethane encapsulation approach, microfluidic or coacervation approaches.

In a second aspect, the present invention relates to a process of making polymeric material having self-healing properties. The process may include the steps of mixing microcapsules containing magnetic nanoparticles in a liquid polymer before curing. The microcapsules in the liquid polymer are guided by magnetic fields to a desired location or locations before curing. Thereafter, the liquid polymer is cured to a solid polymeric material.

The magnetic nanoparticles may be between from about 0.25 to 2 percent (2%) by weight of the microcapsules.

Finally, in a further aspect, the present invention is directed to self-healing polymeric materials synthesized by guiding magnetic microcapsules. Self-healing agents are released from the polymeric material upon fracture thereof.

DETAILED DESCRIPTION OF THE INVENTION

Figure 1:
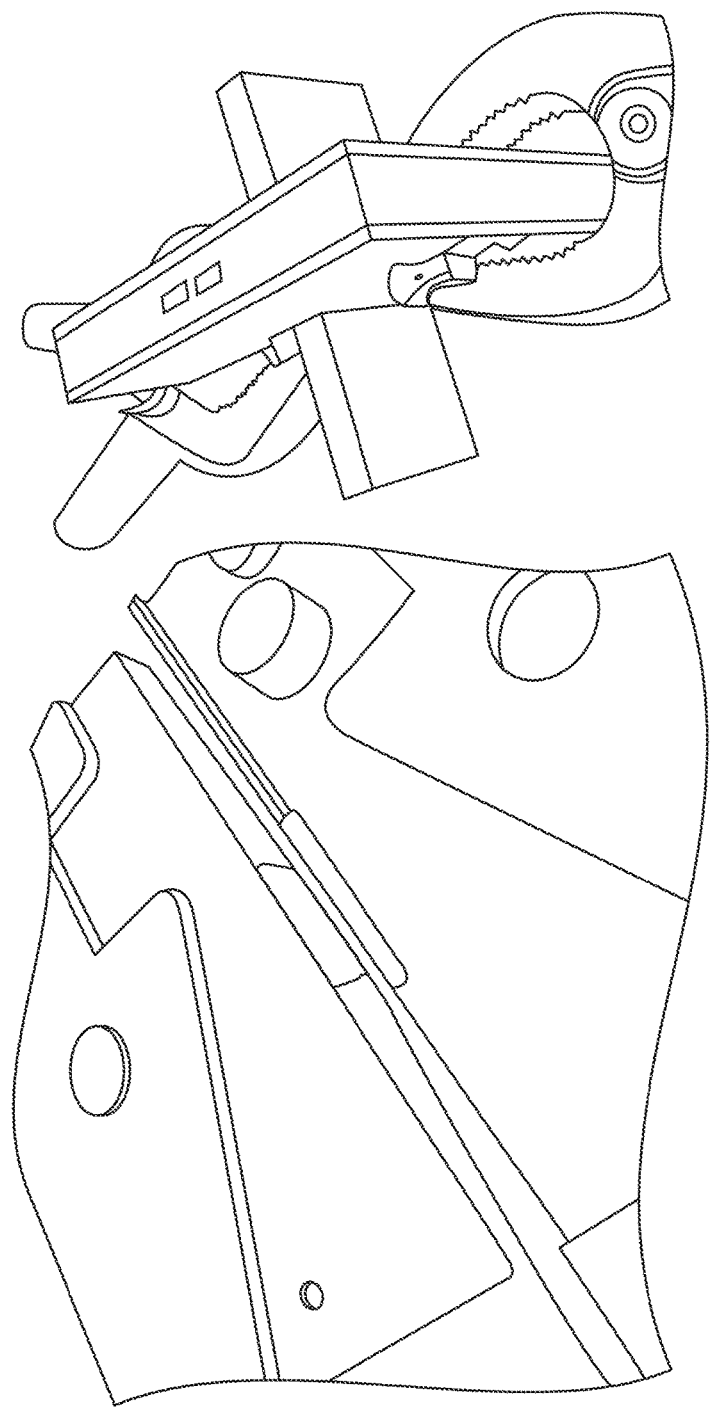
FIG. 1 illustrates a perspective view of molds for a process of manufacturing self-healing polymeric material synthesized by guiding magnetic microcapsules shown with magnets outside the mold in accordance with the present invention.

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

The present invention is directed to a process of making magnetic microcapsules which contain magnetic particles. The process includes a procedure for synthesis of nanoparticles containing magnetic particles. The nanoparticles are suspended in a core material and the core material and nanoparticles are encapsulated in an outer wall in order to form magnetic microcapsules.

Materials and Nanoparticle Synthesis

In one non-limiting example, ferric chloride ($FeCl_3 \cdot 6H_2O$) from Fisher Scientific, ferrous chloride ($FeCl_2 \cdot 4H_2O$) from Alfa Aesar, and ammonium hydroxide ($NH_4OH$) from Sigma-Aldrich were used as the basis for the nanoparticle chemistry. Tetraethyl orthosilicate (TEOS) from Sigma-Aldrich and phenyltriethoxysilane (Gelest, Inc.) were used as the nanoparticle functionalizing agents. Ethylene-maleic anhydride copolymer (EMA, from Vertellus), urea (Sigma-Aldrich), resorcinol (Alfa Aesar), ammonium chloride ($NH_4Cl$, from Arcos), sodium hydroxide (NaOH, from Arcos), 1-octanol (Alfa Aesar), phenyl acetate (Alfa Aesar), and formaldehyde (BDH) were used for the microencapsulation process. EPON 828 resin (Miller Stephenson) was used with the curing agent diethylenetriamine (DETA, Sigma-Aldrich) along with silica spheres (S32 glass bubbles, 3M) to make the base epoxy material.

Nanoparticles were synthesized using a modified version of a procedure described by Zhao et. al. [Zhao Y., Fang J., Wang H., Wang X., and Lin T., "Magnetic Liquid Marbles: Manipulation of Liquid Droplets Using Highly Hydrophobic Fe3O4 Nanoparticles", *Advanced Materials*, 22, 707-710, (2010)]. An iron salt solution was created by the addition of $FeCl_2.4H_2O$ (0.266 g) and $FeCl_3.6H_2O$ (0.723 g) to 20 ml of deionized water. This solution was combined with an equal volume of 4M ammonium hydroxide solution by a high-speed injection process. [Fang M., Ström V., Olsson R. T., Belova L., and Rao K. V., "Rapid mixing: A route to synthesize magnetic nanoparticles with high moment", *Applied Physics Letters*, 99, 222501, (2011)]. The resulting precipitate was separated from the solution with a magnet and washed three times with deionized water. The nanoparticles were coated with a surface functionalized silica coating. Silica coating was carried out via the Stober process. [Stöber W., Fink A., Bohn E. J., "Controlled Growth of Monodisperse Silica Spheres in the Micron Size Range", *Journal of Colloid Interface Science*, 26, 62-69, (1968)]. Nanoparticles were suspended in a solution of 16.7 ml ethanol, 1 ml ammonium hydroxide concentrate, and 5 ml deionized water. Next, 0.8 ml tetraethyl orthosilicate (TEOS) was added to the solution. After mixing overnight, the nanoparticles were separated from the solution with a magnet and washed three times with ethanol. Nanoparticles were then coated in a hydrophobic silane via established methods. [Laurent S., Forge D., Port M., Roch A., Robic C., Vander Elst L., & Muller R. N., "Magnetic iron oxide nanoparticles: Synthesis, stabilization, vectorization, physicochemical characterizations and biological applications", *Chemical Reviews*, 108(6), 2064-2110, (2008)]. The nanoparticles were suspended in 30 ml ethanol and 0.05 ml of ammonium hydroxide concentrate in a round bottom flask under nitrogen protection at 60° C. Lastly, 0.465 ml of phenyltriethoxysilane was added to the solution which was then mixed overnight. The finished nanoparticles were then separated from the solution with a magnet and washed three times with ethanol.

While the nanoparticles were fabricated from iron salt solution in the examples herein, it will be understood that other magnetic materials may be employed within the spirit and scope of the invention.

Microcapsule Synthesis

Microcapsules may be synthesized in a variety of ways, including polyurethane encapsulation, microfluidic or coacervation approaches. In one preferred non-limiting example, microcapsules were created using an in-situ urea-formaldehyde encapsulation technique. [Brown E. N., Kessler M. R., Sottos N. R., & White S. R., "In situ poly(urea-formaldehyde) microencapsulation of dicyclopentadiene", *Journal of Microencapsulation*, 20(6), 719-730, (2003)—process to manufacture]. Batch size was decreased to one-quarter (¼) of a standard sized batch. Differing concentrations of nanoparticles (0.25, 0.33, 0.5, 1, 2 weight percent) were suspended in vials of phenyl acetate core material and vigorously shaken before being added to the microcapsule bath, which was mechanically agitated at 600 rpm. Upon completion of the reaction, the microcapsules were separated from the bath with a magnet and manually washed three times with deionized water. Microcapsules were then vacuum filtered and washed with deionized water and ethanol before drying at room temperature. Microcapsules were sieved before use to break up clumps.

Specimen Manufacturing

Test samples were created using a Tapered Double Cantilevered Beam (TDCB) geometry to measure fracture toughness and healing efficiency of the material. [Brown E. N., "Use of the tapered double-cantilever beam geometry for fracture toughness measurements and its application to the quantification of self-healing", *Journal of Strain Analysis for Engineering Design*, 46, 167-186, (2011)]. A short groove version was used because it has been shown to be suitable for testing the effectiveness of the chosen healing chemistry. [Caruso M. M., Blaiszik B. J., White S. R., Sottos N. R., and Moore J. S., "Full Recovery of Fracture Toughness Using a Nontoxic Solvent-Based Healing System", *Advanced Functional Materials*, 18, 1898-1904, (2008)]. [Rule J. D., Sottos N. R., White S. R., "Effect of Microcapsule Size on the Performance of Self-Healing Polymers", *Polymer*, 48, 3520-3529, (2007)]. As seen in FIG. 1, custom molds for guided specimens were fabricated with a slot extending from the outside surface of the mold down into the groove of the TDCB geometry. A beveled carbon steel strip was placed into the slot to focus the magnetic field supplied by neodymium magnets placed on the outer surface of the mold along the groove in order to guide the microcapsules to the intended fracture location. It will be appreciated that various types of magnets and molds may be utilized within the spirit and scope of the invention.

Control specimens without microcapsule guiding were created using magnetic microcapsules without any magnets on the outside of the molds. All samples were fabricated with EPON 828 epoxy resin heated to 90° C. to decrease viscosity and facilitate the movement of the microcapsules during cure. Diethylenetriamine (DETA) was added in a ratio of 12:100 with the resin, and was also heated to 90° C. prior to being mixed in. Silica powder was also added to the resin of 0.10 wt % to stabilize the fracture during testing. Magnetic microcapsules were added to the epoxy resin in varying weight percentages, and the resulting mixture was immediately poured into the mold while still hot. The specimens were left to cool and cure at ambient temperature for 24 hours, at which point the clamps and magnets were removed and the specimen put in an oven to post-cure for 24 hours at 35° C.

While an epoxy resin was used in the examples, other types of thermosetting resins might be employed within the spirit and scope of the invention.

Fracture Testing

Specimens were removed from the molds after post-cure and pre-cracked with a razor blade just before testing. Specimens were tested in displacement control at a rate of 5 $\mu m \cdot s^{-1}$. Once the fracture propagated along the grove, the specimen was unloaded and removed from the testing machine. Specimens were tested again after 24 hours to assess healing performance. Healing efficiency is defined as the healed fracture toughness over the initial fracture toughness. The TDCB geometry allows for fracture toughness to be directly proportional to the critical load at which the fracture propagates. [Brown, E. N., Use of the tapered double-cantilever beam geometry for fracture toughness measurements and its application to the quantification of self-healing. J Strain Anal Eng Des 2011, 46 (3), 167-186]. This simplifies the equation for healing efficiency to:

$$\eta_{healing} = \frac{K_{IC_{healed}}}{K_{IC_{initial}}} = \frac{P_{healed}}{P_{initial}}$$

Targeted placement is achieved by rendering microcapsules responsive to magnetic fields through the encapsulation of magnetic nanoparticles suspended in the healing agent. The initial model system used magnetic iron-oxide nanoparticles suspended in phenyl acetate within the microcapsule liquid core. Hydrophobic surface-modification of the nanoparticles enabled in-situ encapsulation within a urea-formaldehyde shell.

Microscopy

Figure 2:
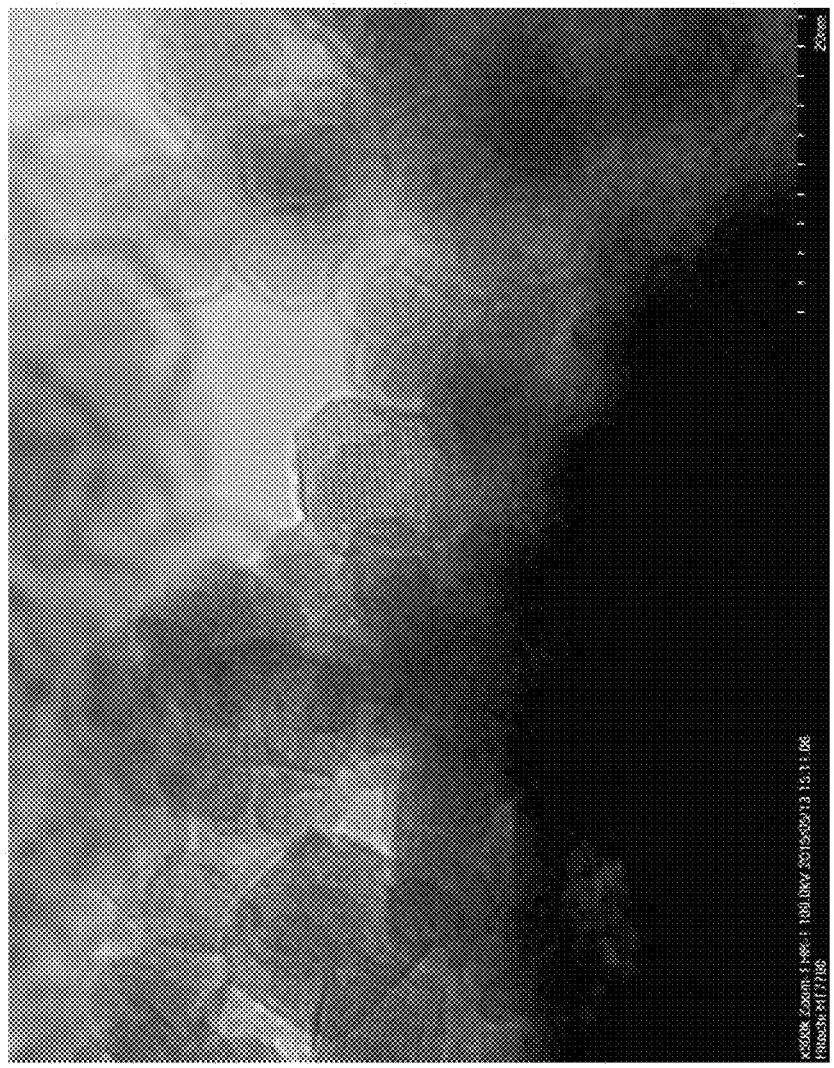
FIG. 2 illustrates a transmission electron microscopy (TEM) showing magnetic nanoparticles of the present invention.

As seen in FIG. 2, Transmission Electron Microscopy (TEM) was performed on the magnetic nanoparticles, showing that they are typically approximately 7 nm in diameter and have a square or hexagonal shape consistent with the isometric hexoctahedral crystal structure of magnetite. [Hamoudeh M., & Fessi H., "Preparation, characterization and surface study of poly-epsilon caprolactone magnetic microparticles", *Journal of Colloid And Interface Science*, 300(2), 584-590, (2006)].

Figure 3:
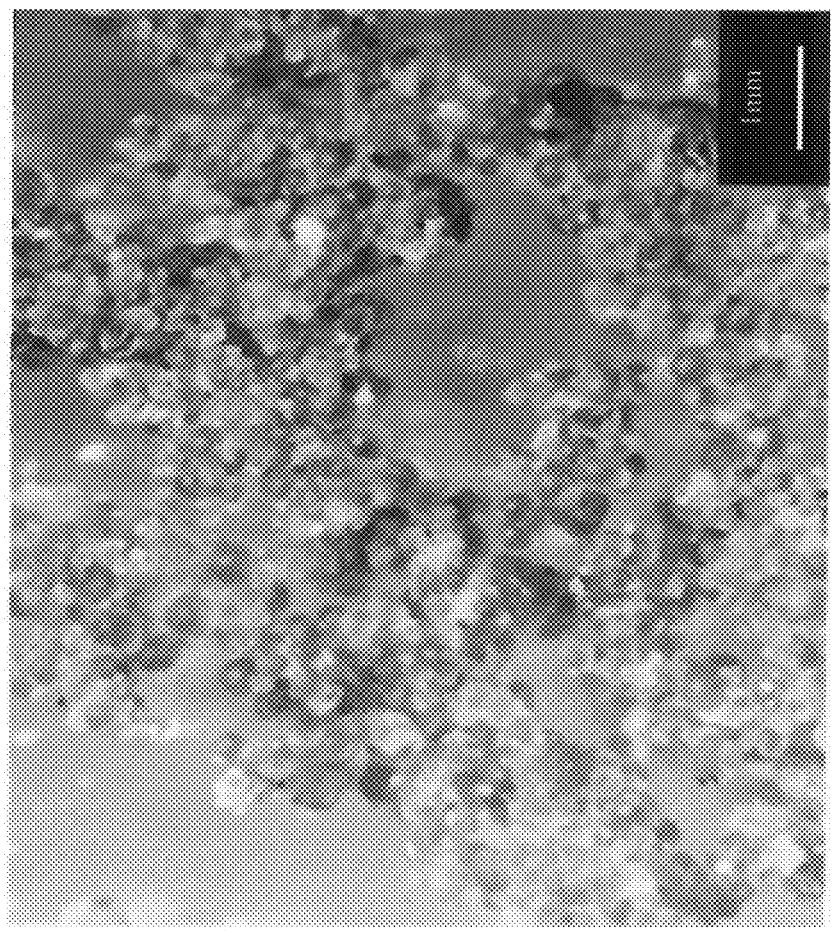
FIG. 3 illustrates an optical microscopy of microcapsules of the present invention with nanoparticles seen through the microcapsule shell walls.
Figure 9:
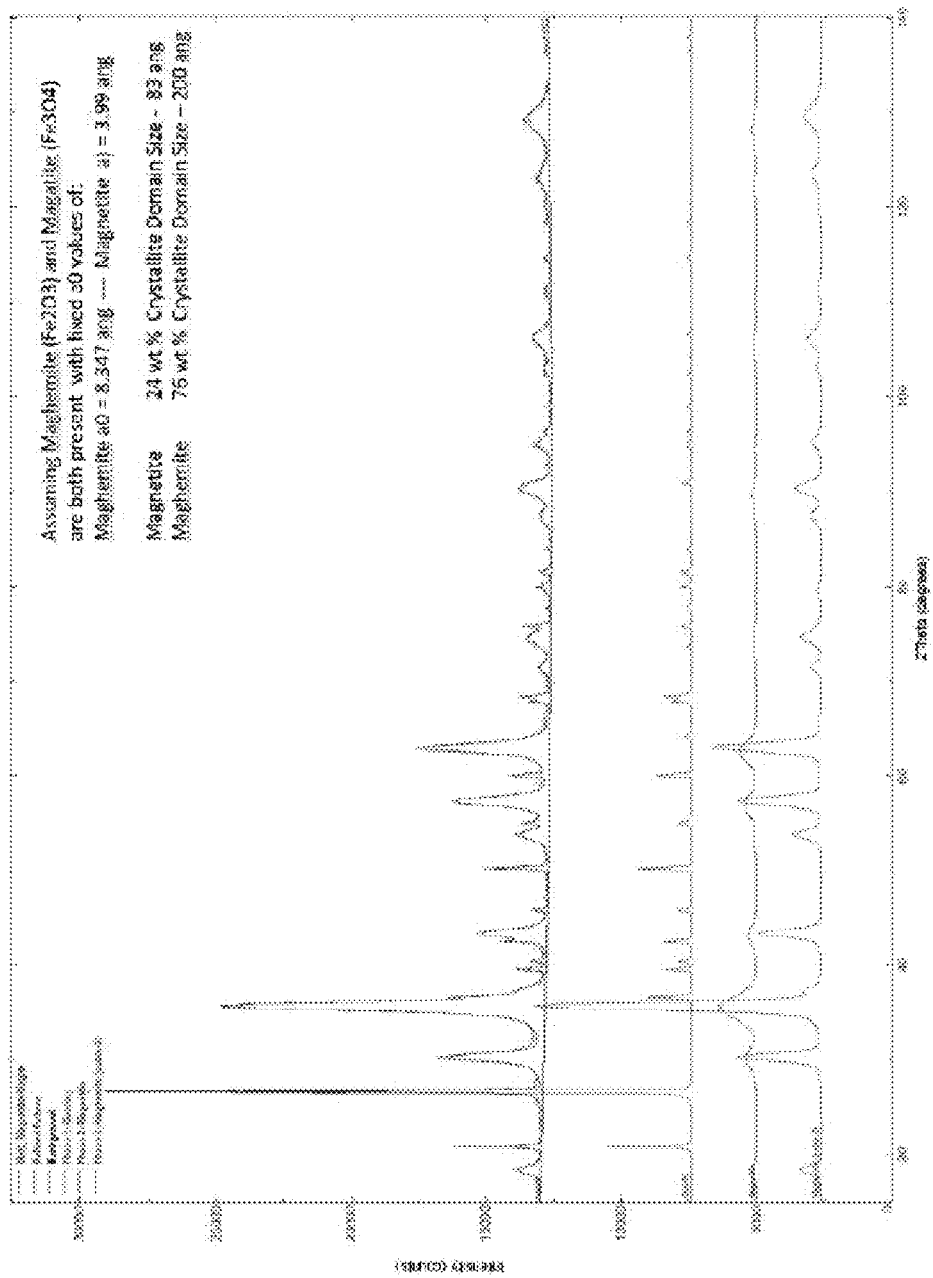
FIG. 9 illustrates an example of a XRD scan on the magnetic nanoparticles, showing the obtained scan (including a quartz reference)

The microcapsules were characterized with optical microscopy after synthesis. As can be seen in FIG. 3, the microcapsules are rather uniform in shape and contain a noticeable amount of the nanoparticles in the core. X-ray diffraction was performed on the nanoparticles to determine crystalline structure and confirm exact particle type. See FIG. 9. Crystal structure was found to be consistent with a mixture of magnetite (~24 wt %) and maghemite (~76 wt %). This solid phase mix of magnetite and maghemite likely started as a high concentration of magnetite which experienced an ingrowth of maghemite via topotactic oxidation when exposed to air. [Aliahmad, M.; Nasiri Moghaddam, N., Synthesis of maghemite ($\gamma$-$Fe_2O_3$) nanoparticles by thermal-decomposition of magnetite ($Fe_3O_4$) nanoparticles. Materials Science-Poland 2013, 31 (2), 264-268]. Based on this composition, the critical diameter of the nanoparticles is expected to be in the range 70-150 nm. [Stephen, Z. R.; Kievit, F. M.; Zhang, M., Magnetite Nanoparticles for Medical MR Imaging. Materials today (Kidlington, England) 2011, 14 (7-8), 330-338]. [Brice-Profeta, S.; Arrio, M. A.; Tronc, E.; Menguy, N.; Letard, I.; Cartier dit Moulin, C.; Noguès, M.; Chanéac, C.; Jolivet, J. P.; Sainctavit, P., Magnetic order in—nanoparticles: a XMCD study. Journal of Magnetism and Magnetic Materials 2005, 288, 354-365]. In this study, the particles have a measured diameter of 7 nm and therefore should be a single domain. Additionally, the particles are below the approximately 20 nm and therefore can be considered paramagnetic. [Stephen, Z. R.; Kievit, F. M.; Zhang, M., Magnetite Nanoparticles for Medical MR Imaging. Materials today (Kidlington, England) 2011, 14 (7-8), 330-338]. These properties likely have little effect on the ability to use them to render microcapsules responsive to magnetic fields. Any variation due to temperature change or particle agglomeration is small. A magnetized razorblade can be used to manipulate the nanoparticles floating within the microcapsules from the outside, and crush tests confirm that the microcapsules contain liquid.

Figure 5:
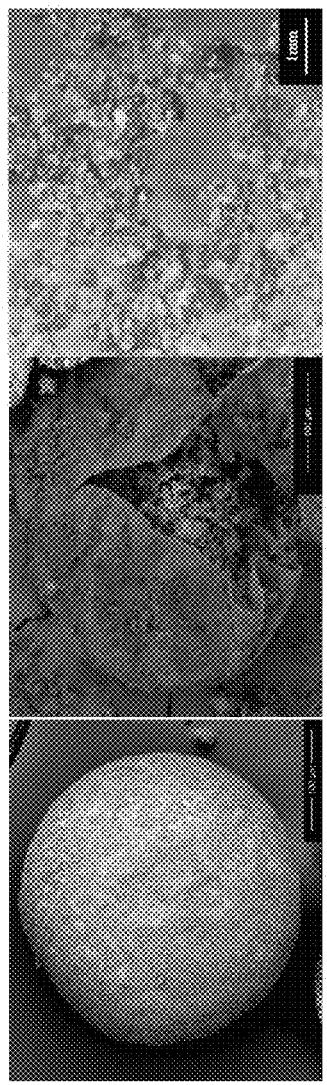
FIG. 5 illustrates an optical microscopy of fracture surfaces of guided specimens containing microcapsules.
Figure 10:
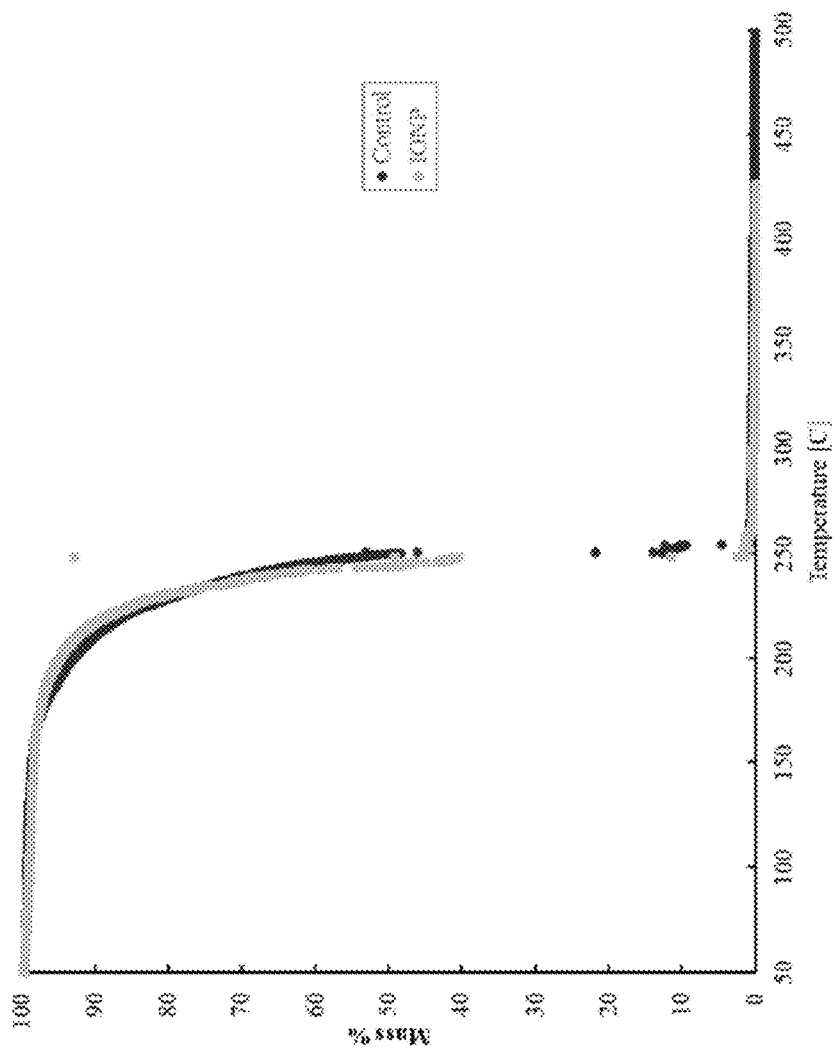
FIG. 10 illustrates a graph of microcapsules containing iron-oxide magnetic nanoparticles (IONP) and microcapsules not containing nanoparticles.
Figure 11:
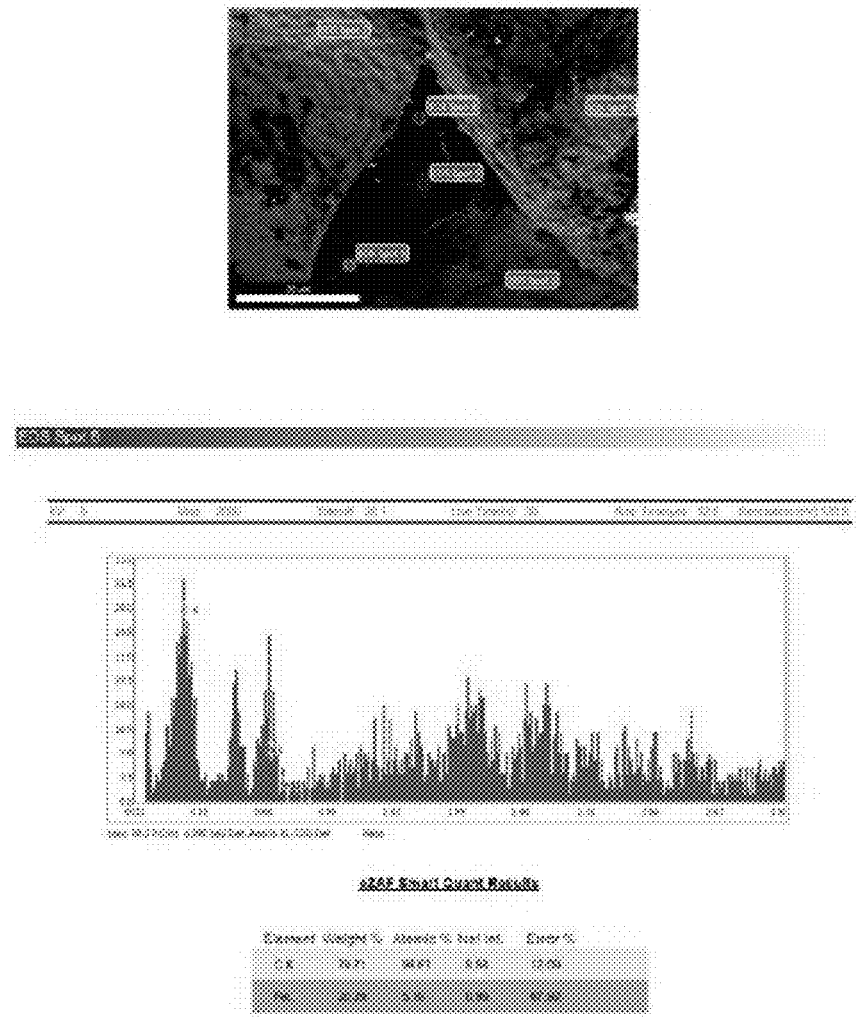
FIG. 11 illustrates energy-dispersive X-ray spectroscopy (EDS) analysis of microcapsules.

While free nanoparticles were observed floating within the microcapsules, it is energetically favorable for the nanoparticles to congregate at the oil-water interface during encapsulation. [Binks, B. P., Particles as surfactants—similarities and differences. Current Opinion in Colloid & Interface Science 2002, 7 (1-2), 21-41]. Therefore, it is likely that some nanoparticles are also embedded within the microcapsule shell wall. Microcapsules were stable, and crush tests confirm that they contain liquid, even after several months of refrigerated storage. The stability of the capsules was studied using TGA with a temperature ramp from 25 C to 500° C. at 10° C./min. The magnetic microcapsules were found to have the initial mass loss occur at a higher temperature, X vs Y (see FIG. 10). This behavior indicates that the nanoparticles increase the barrier properties over non-magnetic microcapsules, potentially by having a toughening effect on the microcapsule shell wall. The microcapsules synthesized for this study had an average diameter of 171±55 µm with a shell wall thickness of 141±20 nm. These values were determined from optical and SEM images (FIG. 5) and are consistent with measurements from previous research on non-magnetic urea-formaldehyde microcapsules. [Brown, E. N.; Kessler, M. R.; Sottos, N. R.; White, S. R., In situ poly(urea-formaldehyde) microencapsulation of dicyclopentadiene. Journal of Microencapsulation 2003, 20 (6), 719-30]. The presence of the nanoparticles was also confirmed using EDS analysis (Energy-dispersive X-ray spectroscopy), which indicated a high concentration of iron in the particles located within the core of crushed microcapsules, values not seen when EDS is performed on non-magnetic microcapsules (FIG. 11). Atomic Absorption Spectroscopy (AAS) was performed to more accurately determine how the measured iron content of the microcapsules compared with the amount added during synthesis. The iron content was determined to be in the range 0.105%-0.302%. This compares well to the 0.23% of Fe that should be present in a sample that had 0.33% magnetite or maghemite by weight added during the synthesis of the microcapsules.

Figure 4A:
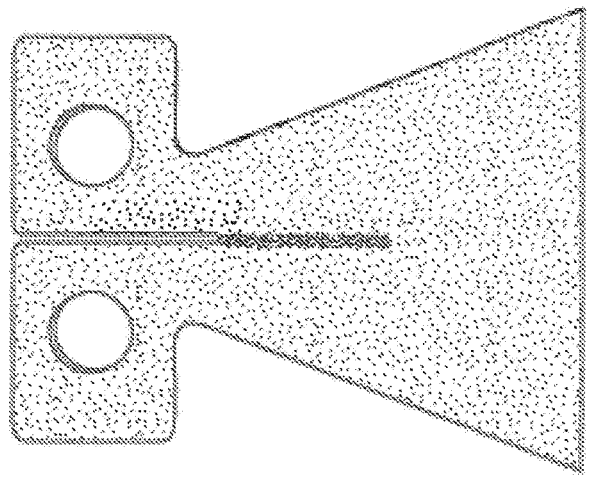
FIG. 4 illustrates a control specimen and a guided specimen having guided microcapsules and a guided specimen having complex shapes utilizing the teachings of the present invention.
Figure 4B:
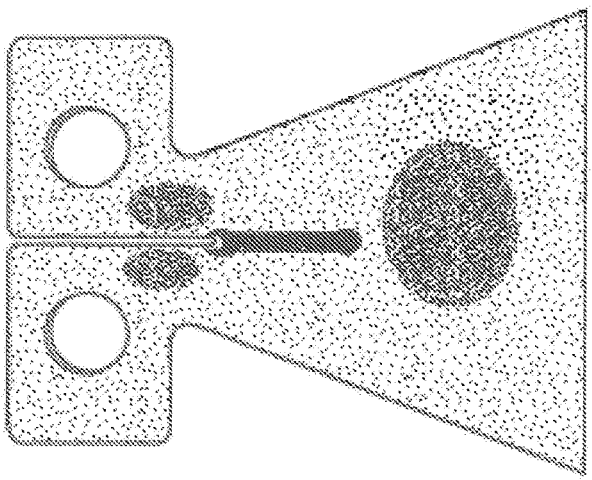
Figure 4C:
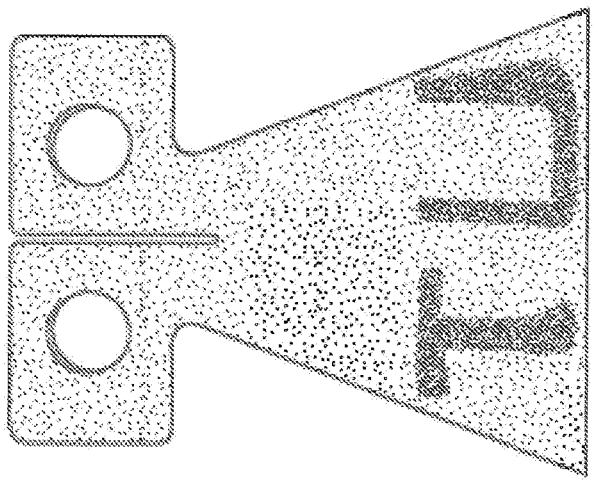

Microcapsules were guided to the center of thermoset epoxy tapered double-cantilever beam (TDCB) specimens using permanent magnets on the exterior of the mold. Mild steel strips were embedded within the mold to enhance local magnetic field strength and improve the precision of the microcapsule placement. Control specimens of identical geometry were fabricated by uniformly dispersing the same microcapsules throughout the material without guiding. Visual inspection of guided specimens shows that the microcapsules are highly concentrated in the intended location along the TDCB groove. FIG. 4 illustrates the difference between uniform microcapsule dispersion (FIG. 4a) and microcapsule guiding (FIG. 4b). This approach has sufficient fidelity to manipulate the location of microcapsules into a variety of complex shapes (FIG. 4c).

Figure 6:
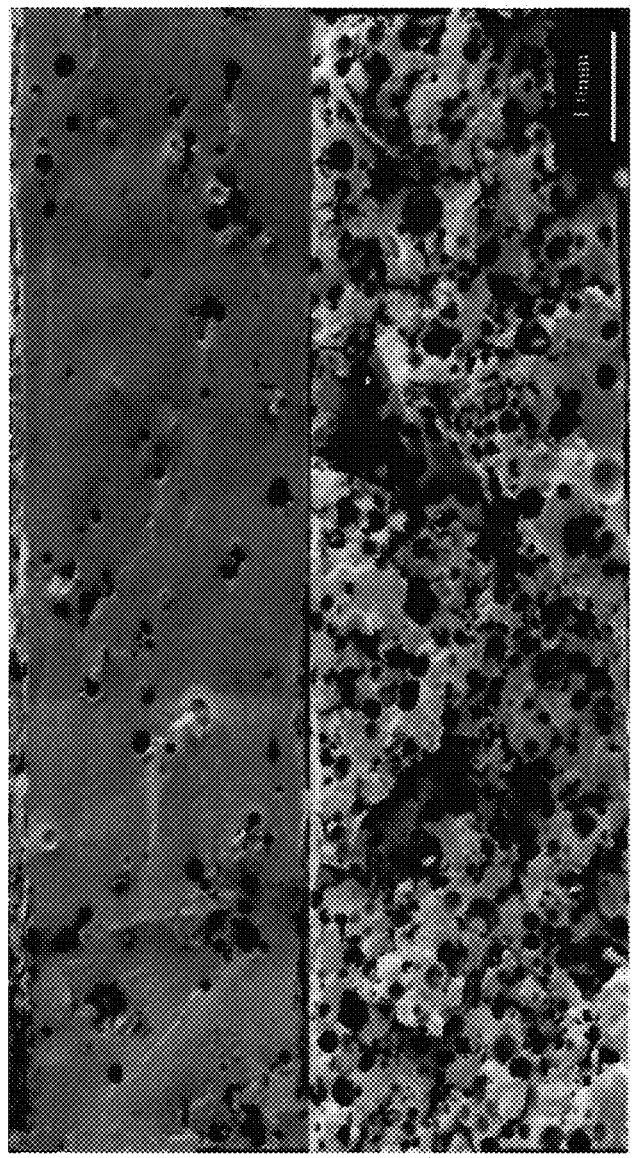
FIG. 6 illustrates scanning electron microscopy of the fracture surfaces of a control specimen and a guided specimen employing the teachings of the present invention.

After fracture testing, SEM was used to analyze the position and concentration of microcapsules locally along the fracture surface. A representative set of SEM images of control and guided specimens, both containing 1 nominal wt % microcapsules, is shown in FIG. 6. For these samples, area-base estimates of apparent volume fraction of microcapsules gave 1.8 vol % for the control specimen and 14.8 vol % for the guided specimen.

Figure 12:
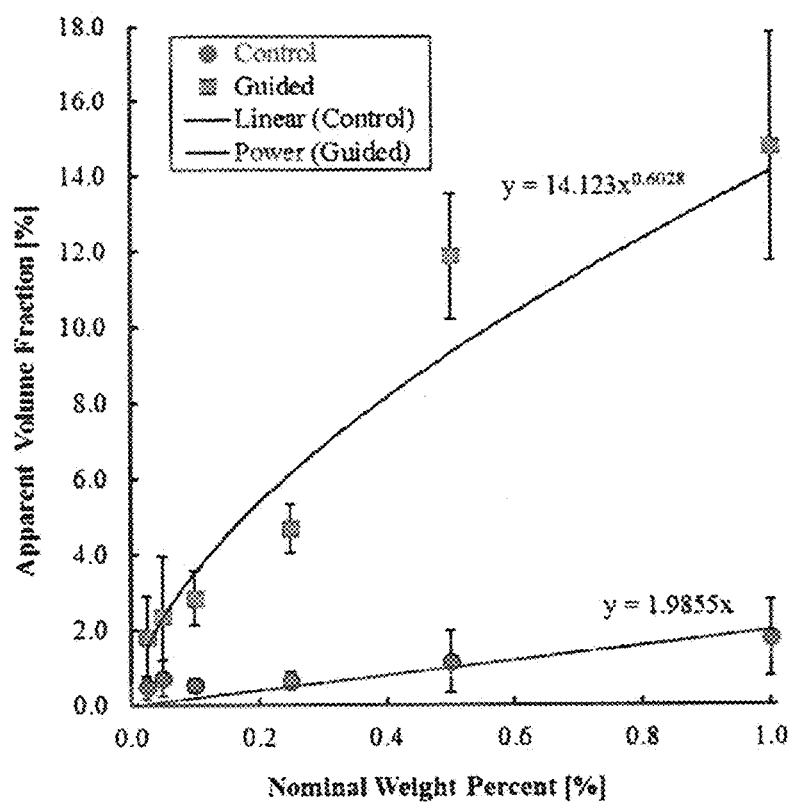
FIG. 12 illustrates a graph of nominal weight percent (amount added to the material in bulk) versus apparent volume fraction.

An order of magnitude increase in local microcapsule concentration can be achieved using magnetic guiding. This trend continues even as nominal microcapsule concentration is decreased from 1 wt % down to 0.025 wt %, with controls decreasing linearly and guided specimens following a power-law curve, as illustrated in FIG. 12. This shows a high degree of control over the location of even small numbers of microcapsules. SEM analysis also indicated that microcapsules tend to congregate along the outer face of the groove of guided specimens. This localization is expected due to the distribution of magnetic field strength through the sample thickness. As nominal concentration of microcapsules increases, the microcapsules will pile up and eventually fill the entire thickness of the specimen from the outside inward.

Increasing the nanoparticle concentration within the microcapsules also leads to a more effective filling of the fracture plane, as the presence of more magnetic nanoparticles within the core increases the magnetic force on the microcapsules. This tends to drive more microcapsules to the magnetized region. Larger microcapsules also appear to be more easily guided than smaller microcapsules, again, likely due to increased magnetic force caused by the presence of a greater number of nanoparticles. In all cases, the application of a localized magnetic field during cure guided the microcapsules toward the groove, increasing the concentration near the fracture location when compared to control specimens.

Figure 13:
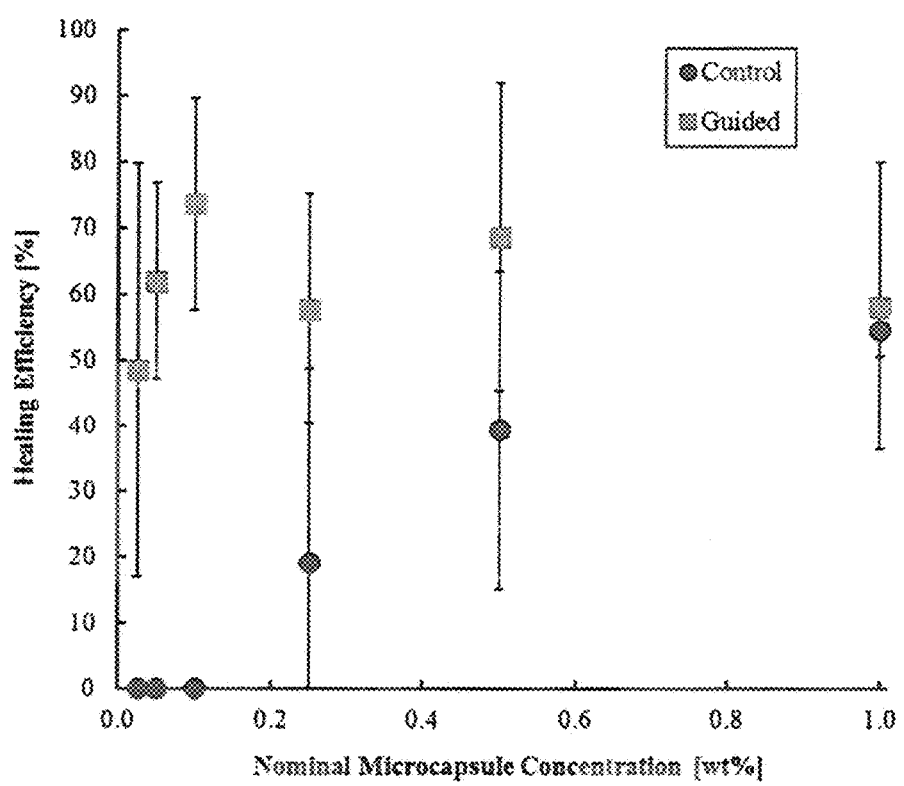
FIG. 13 illustrates a graph of nominal microcapsule weight percent verses healing efficiency for both control and guided groups.

Self-healing functionality was assessed using a short groove tapered double-cantilever beam (TDCB) specimen geometry. Previous research has shown that this geometry is suitable for investigating solvent-based healing. Nominal microcapsule weight percentages were varied to determine the impact of microcapsule concentration on self-healing efficiency and consistency. FIG. 13 illustrates a graph of nominal microcapsule wt % vs. healing efficiency for control and guided groups. The healing efficiency for control specimens falls off rapidly as the nominal microcapsule concentration goes below 1 wt %. Eventually, control specimens fail to heal, indicating there was not a sufficient concentration of microcapsules in the fracture plane. In contrast, guided specimens show good healing efficiency for all microcapsule weight percentages tested, remaining relatively constant. Healing efficiency even exceeds 100% for some individual tests. This performance is consistent with previous research using solvent-based healing. Previous work reports only peak load for a phenyl acetate healing chemistry. Therefore, a direct comparison to the results in this study cannot be made, as silica particulate was required to stabilize the fracture behavior of the epoxy at the low microcapsule concentrations studied in the present work. The closest comparison can be found in a study by Caruso et al. that demonstrated a healing efficiency of 50% for a pure ethyl phenyl acetate system. These values are comparable to the values achieved in situ using phenyl acetate.

The healing efficiency of guided specimens converges to that of control specimens as the nominal concentration increases to 1 wt % (FIG. 13). This upper limit is likely due to the fracture plane becoming fully saturated, with additional healing agent not providing any benefit. Two-way ANOVA testing confirms that there is a significant difference between the control and guided specimen groups (P=4.3× $10^{-10}$), weight percentages (P=0.0012), and interaction between the groups and weight percentages (P=0.0001). In addition, baseline control tests were run at a nominal microcapsule concentration of 1 wt % using the same microcapsule chemistry, but without the presence of the magnetic nanoparticles. Based on the healing efficiency results from this test, the addition of nanoparticles to the microcapsules appears to have no impact on the performance of this healing chemistry (P=0.89). Additionally, there was no statistical difference in either the virgin fracture toughness (P=0.595) or the healed fracture toughness (P=0.834) between the specimens with microcapsules that contain nanoparticles and specimens with microcapsules that did not contain nanoparticles, indicating the nanoparticles likely do not alter the material properties. This result is expected because the healing chemistry does not result in the formation of any new polymer. Solvent-based healing occurs primarily though diffusion and chain entanglement rather than through adhesive bonding of a polymerized healing agent. Because of the nature of the healing processes, it is unlikely that the nanoparticles bond to the matrix during healing. This is additionally supported by the observation that healing efficiencies for both guided and control samples are approximately equal in the plateau region of 0.5-1.0 wt %, even though a larger number of nanoparticles are present in the healed region of guided samples. This implies that the nanoparticles are not providing any additional mechanical reinforcement.

Figure 14:
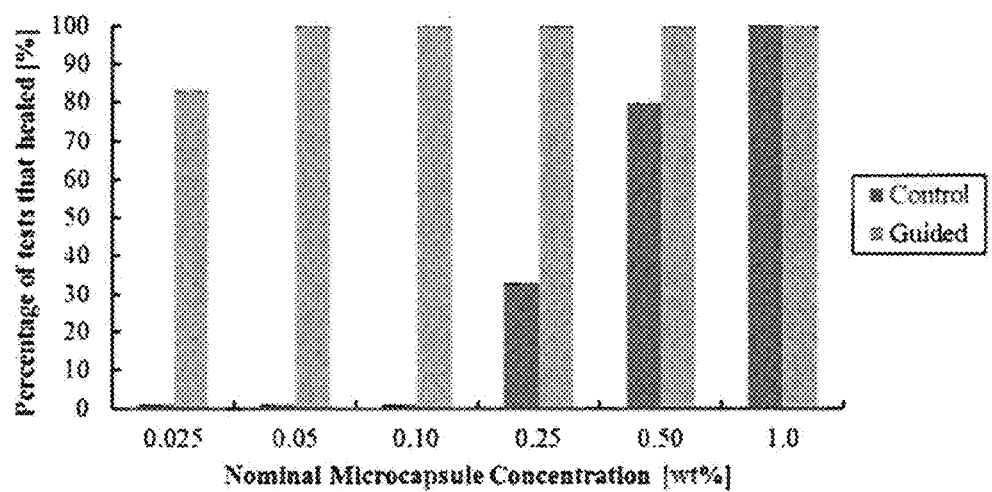
FIG. 14 illustrates a graph of how many tests within each group exhibited healing behavior.

The number of successful healing events was quantified for both control and guided groups, and this comparison is shown in FIG. 14. The graph shows how many tests within each group exhibited healing behavior. In this figure, a successful healing event was defined as any test showing a healing efficiency greater than 0%. As nominal microcapsule weight percent is decreased, fewer control specimens exhibit healing, with no healing occurring when nominal microcapsule concentration falls below 0.1 wt %. In contrast, guided specimens exhibit more consistent healing, with 100% success until 0.025 nominal wt % when one specimen did not heal. This improvement in consistency is desirable for structural components that are mission-critical or do not have redundancy in the load path. From this study, the lower threshold of microcapsule concentration required to achieve self-healing using the proposed guiding approach could be estimated. The lowest nominal microcapsule concentration to achieve any healing in control specimens was 0.25 wt %. Using the power-law relationship illustrated in FIG. 12, this lower limit of 0.25 wt % can be locally achieved in the fracture plane of guided specimens using a nominal concentration of only 0.004 wt %. This represents the theoretical minimum amount of microcapsules that can be added to a specimen and still achieve healing using microcapsule guiding. By this assessment, microcapsule concentration can be reduced by orders of magnitude below the minimum value of 1.25 wt % estimated by Rule et al. in previous work. Using the average number and size of microcapsules present in the fracture plane, this estimate corresponds to a minimum volume of healing agent delivered per unit crack area of 0.1 $\mu L/cm^2$, which is also less than the value estimated by Rule et al. using the same short groove TDCB geometry.

Quasi-Static Fracture Testing and Self-Healing Performance

Figure 7:
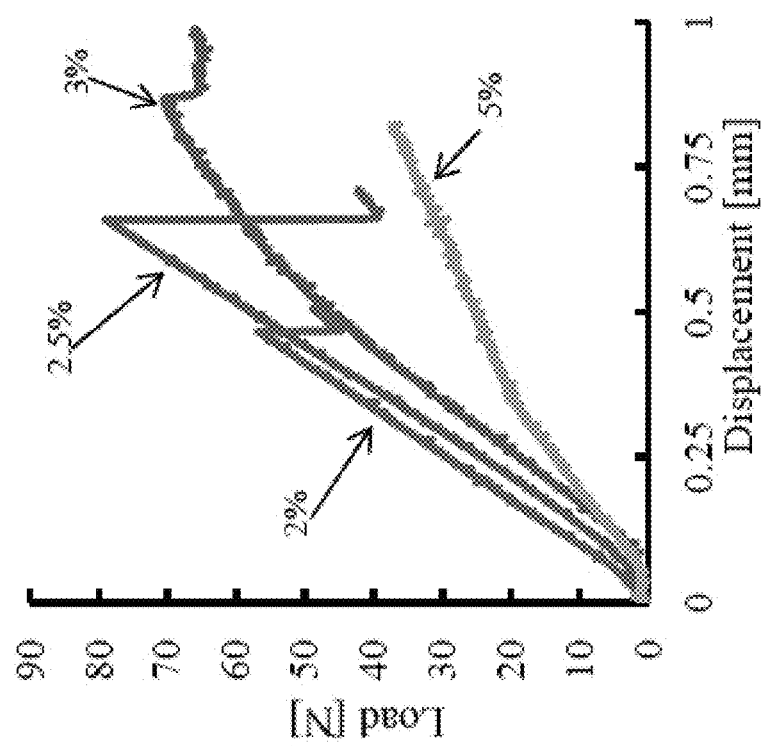
FIG. 7 illustrates a graph showing displacement in relation to load for fracture testing of guided specimens containing microcapsules at different percentages by weight.

A series of quasi-static fracture tests were performed using guided specimens with varying weight percentages of microcapsules. The results are shown in FIG. 7. An increase in nominal microcapsule concentration initially causes an increase in fracture toughness from 2-2.5% microcapsules by weight, as expected from prior work. [Brown E. N., White S. R., Sottos N. R., "Microcapsule induced toughening in a self-healing polymer composite", *Journal of Materials Science*, 39, 1703-1710, (2004)]. This increase is followed by a transition from a brittle fracture failure mode to a non-linear fracture as the nominal microcapsule weight percent approaches 3-5%.

Figure 8:
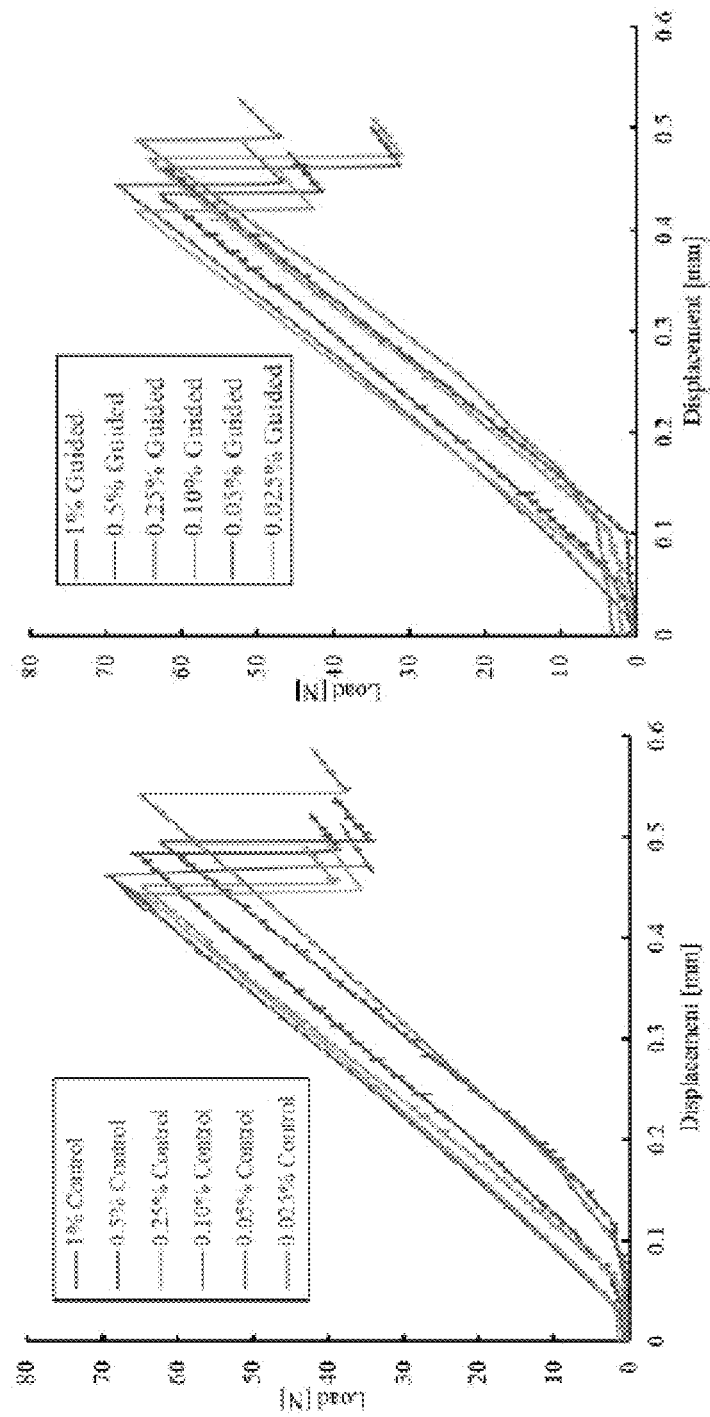
FIG. 8 illustrates graphs of load displacement versus load for fracture testing comparing control specimens and guided specimens utilizing the teachings of the present invention.

This is likely a result of very high local concentrations of microcapsules, which weaken the material by displacing epoxy in the test region. This can occur at relatively low nominal concentrations for guided specimens, as local concentrations of microcapsules along the outer edge of the TDCB groove can approach 30-40 vol % for guided specimens at 1 nominal wt %. The fracture toughness for control specimens remained unchanged for the low weight percentages (0.025%-1.0%) that comprise the bulk of this work (FIG. 8). This result is expected from previous investigations on microcapsule toughening by Brown et al. Guided specimens also had constant fracture toughness in the low weight percentage samples (0.025%-1.0%), with no statistical difference in fracture toughness being observed across all weight percentages (P=0.07). This behavior may be the result of the location of the microcapsules. As shown in FIG. 6, the microcapsules in guided samples are concentrated on the outer edge of specimens, rather than uniformly distributed through the thickness. This dumping of the microcapsules likely inhibits toughening mechanisms that would otherwise be at play. However, it is noteworthy that edge dumping does not result in a lower fracture toughness compared to controls. This result indicates that microcapsule guiding can be used to increase healing efficiency without impacting other material properties.

To summarize the testing, microcapsules containing magnetic nanoparticles were synthesized and incorporated into self-healing epoxy specimens for fracture testing. The microcapsules were successfully guided to the intended fracture location using magnetic fields. SEM of the fracture surface showed an estimated apparent volume fraction of 4.1% for controls and 43% for guided specimens both at 4% microcapsule nominal weight percent. Specimens containing guided microcapsules displayed an increase in fracture toughness over control specimens when low weight percentages of microcapsules were used (less than 3% by weight). At higher microcapsule weight percentages, guided specimens showed a transition to tearing failure mode as opposed to the brittle fracture exhibited by control specimens. These same trends were observed as nanoparticle concentration was increased within the microcapsules at fixed microcapsules weight percentages. Successful self-healing was achieved in guided specimens, with a potential increase in performance over controls.

Magnetically guided microcapsules used to achieve self-healing with a fraction of the healing components required using traditional self-healing approaches. Microcapsules are rendered responsive to magnetic fields by suspending magnetic nanoparticles in a core material. The nanoparticles are surface-modified to enable encapsulation within a core. Magnetic fields are used to guide the microcapsules to an expected fracture location or locations. This guiding method achieves an order of magnitude increase in local microcapsule concentration over uniform distribution of microcapsules. Additionally, the observed healing is both more consistent and significantly higher than that of uniform distribution of microcapsules.

Whereas, the devices and methods have been described in relation to the drawings and claims, it should be understood that other and further modifications, apart from those shown or suggested herein, may be made within the spirit and scope of this invention.

What is claimed is:

1. A process of making magnetic microcapsules, which process comprises:
   coating magnetic particles with a hydrophobic material coating to form nanoparticles;
   suspending said nanoparticles in a core material; and
   encapsulating said core material and said nanoparticles in an outer wall to form magnetic microcapsules.

2. The process of making magnetic microcapsules as set forth in claim 1 wherein said magnetic particles are micron or smaller size magnetic particles.

3. The process of making magnetic microcapsules as set forth in claim 1 wherein said magnetic particles are fabricated from iron salt solution.

4. The process of making magnetic microcapsules as set forth in claim 1 wherein said hydrophobic material coating is a surface-functionalized silica coating.

5. The process of making magnetic microcapsules as set forth in claim 1 wherein said hydrophobic material coating is hydrophobic silane.

6. The process of making magnetic microcapsules as set forth in claim 1 wherein said outer wall is formed by microencapsulation.

7. The process of making magnetic microcapsules as set forth in claim 1 wherein said nanoparticles are from between about 0.25 percent (0.25%) to 2 percent (2%) by weight of said microcapsules.

8. A process of making polymeric material having self-healing properties, said process comprising:
   mixing microcapsules containing magnetic nanoparticles in a liquid polymer before curing;
   guiding said microcapsules in said liquid polymer before curing; and
   curing said liquid polymer to a solid polymeric material.

9. The process of making polymeric material having self-healing properties as set forth in claim 8 wherein said microcapsules in said liquid polymer are guided before curing by magnetic fields.

10. The process of making polymeric material having self-healing properties as set forth in claim 8 wherein said magnetic nanoparticles are from between about 0.25 percent (0.25%) to 2 percent (2%) by weight of said microcapsules.

11. The process of making polymeric material having self-healing properties as set forth in claim 8 wherein said magnetic nanoparticles are coated with a hydrophobic material coating.

12. The process of making polymeric material having self-healing properties as set forth in claim 8 including initially forming said microcapsules from said nanoparticles suspended in a core material and encapsulating in an outer wall.

13. The process of making polymeric material having self-healing properties as set forth in claim 8 wherein said step of guiding said microcapsules in said liquid polymer achieves multiple times concentration of microcapsules at a guided location versus uniform distribution of said microcapsules.

14. A process to self-heal material fractures, which process comprises:
   guiding magnetic microcapsules in a liquid polymer;
   curing said liquid polymer to a solid polymeric material; and
   releasing a healing agent from said microcapsules upon fracture of said polymeric material.

15. The process to self-heal material fractures as set forth in claim 14 wherein said magnetic microcapsules in said liquid polymer are guided before curing by magnetic fields.

16. The process to self-heal material fractures as set forth in claim 14 including initially forming said magnetic microcapsules from magnetic nanoparticles suspended in a core material and encapsulating in an outer wall.

17. The process to self-heal material fractures as set forth in claim 14 wherein said step of guiding magnetic microcapsules in said liquid polymer achieves multiple times concentration of microcapsules at a guided location versus uniform distribution of said microcapsules.

* * * * *